(12) United States Patent
Morello

(10) Patent No.: US 7,175,588 B2  
(45) Date of Patent: Feb. 13, 2007

(54) METHOD AND SYSTEM FOR DETECTING VENTRICULAR COLLAPSE

(75) Inventor: Gino F Morello, Leonia, NJ (US)

(73) Assignee: Micromed Technology, Inc., Houston, TX (US)

( * ) Notice: Subject to any disclaimer, the term of this patent is extended or adjusted under 35 U.S.C. 154(b) by 232 days.

(21) Appl. No.: 10/501,275

(22) PCT Filed: Jan. 8, 2003

(86) PCT No.: PCT/US03/00516

§ 371 (c)(1),  
(2), (4) Date: Jul. 8, 2004

(87) PCT Pub. No.: WO03/057013

PCT Pub. Date: Jul. 17, 2003

(65) Prior Publication Data

US 2005/0004418 A1    Jan. 6, 2005

Related U.S. Application Data

(60) Provisional application No. 60/346,555, filed on Jan. 8, 2002.

(51) Int. Cl.
| | |
|---|---|
| A61N 1/362 | (2006.01) |
| A61B 5/02 | (2006.01) |
| A61M 1/10 | (2006.01) |
| A61M 37/00 | (2006.01) |
| A61M 31/00 | (2006.01) |

(52) U.S. Cl. ............... 600/17; 600/16; 600/504; 600/505; 600/508; 623/3.1; 604/6.11; 604/67

(58) Field of Classification Search ............ 600/16–17, 600/508, 504–505; 604/6.11, 67; 623/3.1  
See application file for complete search history.

(56) References Cited

U.S. PATENT DOCUMENTS

| 4,499,534 | A | * | 2/1985 | Schnetzka et al. ........... 363/129 |
| 5,888,242 | A | * | 3/1999 | Antaki et al. ............... 623/3.28 |
| 6,183,412 | B1 | * | 2/2001 | Benkowski et al. .......... 600/16 |
| 6,991,595 | B2 | * | 1/2006 | Burke et al. ................ 600/17 |

* cited by examiner

Primary Examiner—Robert E. Pezzuto  
Assistant Examiner—Natasha Patel  
(74) Attorney, Agent, or Firm—Locke Liddell & Sapp LLP (57) ABSTRACT

A pump system includes an implantable pump including a motor having a rotor and a stator. The stator includes a plurality of stator windings, and a motor controller is coupled to the motor to energize the windings so as cause the rotor to turn. A time-based system parameter of the pump is sampled and the system parameter is analyzed to calculate a suction probability index that provides an indication of the imminence of ventricle collapse.

34 Claims, 6 Drawing Sheets

METHOD AND SYSTEM FOR DETECTING VENTRICULAR COLLAPSE

CROSS-REFERENCE TO RELATED APPLICATION

This application claims the benefit of U.S. Provisional Patent Application Ser. No. 60/346,555, filed on Jan. 8, 2002, the entire contents of which is incorporated by reference.

BACKGROUND OF THE INVENTION

1. Field of the Invention

The invention relates generally to implanted or implantable blood pump systems, and more specifically, to a method and system for detecting the onset and/or presence of ventricular collapse associated with such pumps.

2. Description of Related Art

Generally, implantable blood pump systems are employed in either of two circumstances. First an implantable blood pump may completely replace a human heart that is not functioning properly, or second, an implantable blood pump may boost blood circulation in patients whose heart is still functioning although pumping at an inadequate rate.

For example, U.S. Pat. No. 6,183,412, which is commonly assigned and incorporated herein by reference in its entirety, discloses a ventricle assist device (VAD) commercially referred to as the "DeBakey VAD®". The VAD is a miniaturized continuous axial-flow pump designed to provide additional blood flow to patients who suffer from heart disease. The device is attached between the apex of the left ventricle and the aorta. Proper blood flow through the device depends on an adequately filled ventricle and a positive differential pressure between the inlet and the outlet of the VAD pump.

Since this device produces flow continually and actively fills, it has the potential to create low pressure at the inflow in order to produce flow. "Excess Suction" occurs when the pressure in the inflow cannula decreases significantly—the pump begins to "suck" the ventricle closed, which would greatly reduce the pumping capability of the native heart and VAD. Decreasing the VAD's speed during an excess suction condition would allow the ventricle to refill, and normal blood flow to resume. Additionally, the detection of ventricular collapse and the ability to automatically adjust the pump's speed may aid in maintaining correct blood flow to the patient.

Excess suction may be caused by occlusion of the tip of the inflow cannula or by completely emptying the ventricle (ventricular collapse). In known pump systems, sustained excess suction typically triggers a diagnostic alarm on the pump controller. However, it would be desirable to detect the onset of suction prior to any physiologic effect. Additionally, it is typical of known methods that attempt to detect the onset or presence of ventricular collapse to use a binary "suction detect" flag when the onset of suction is believed to have been discovered. Information in addition to a simple binary indicator, however, is desirable as it would allow a physician or technician to make a more precise diagnosis.

The present invention addresses shortcomings associated with the prior art.

SUMMARY OF THE INVENTION

In one aspect of the present invention, an implantable pump system includes an implantable pump including a motor having a rotor and a stator. The stator includes a plurality of stator windings, and a motor controller is coupled to the motor to energize the windings so as cause the rotor to turn. A time-based system parameter of the pump is sampled and the system parameter is analyzed to calculate a suction probability index that provides an indication of the imminence of ventricle collapse.

In certain embodiments of the invention, the pump system includes a processor that is programmed to analyze the parameter and calculate the suction probability index. The system parameter may include, for example, the pump current, power, speed, etc. Further, the pump system may include an implantable flow sensing device, wherein the pump flow rate may be sampled and analyzed. In accordance with other aspects of the invention, various frequency domain and time domain techniques are disclosed for analyzing the system parameters to calculate the suction probability index.

BRIEF DESCRIPTION OF THE DRAWINGS

Other objects and advantages of the invention will become apparent upon reading the following detailed description and upon reference to the drawings in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
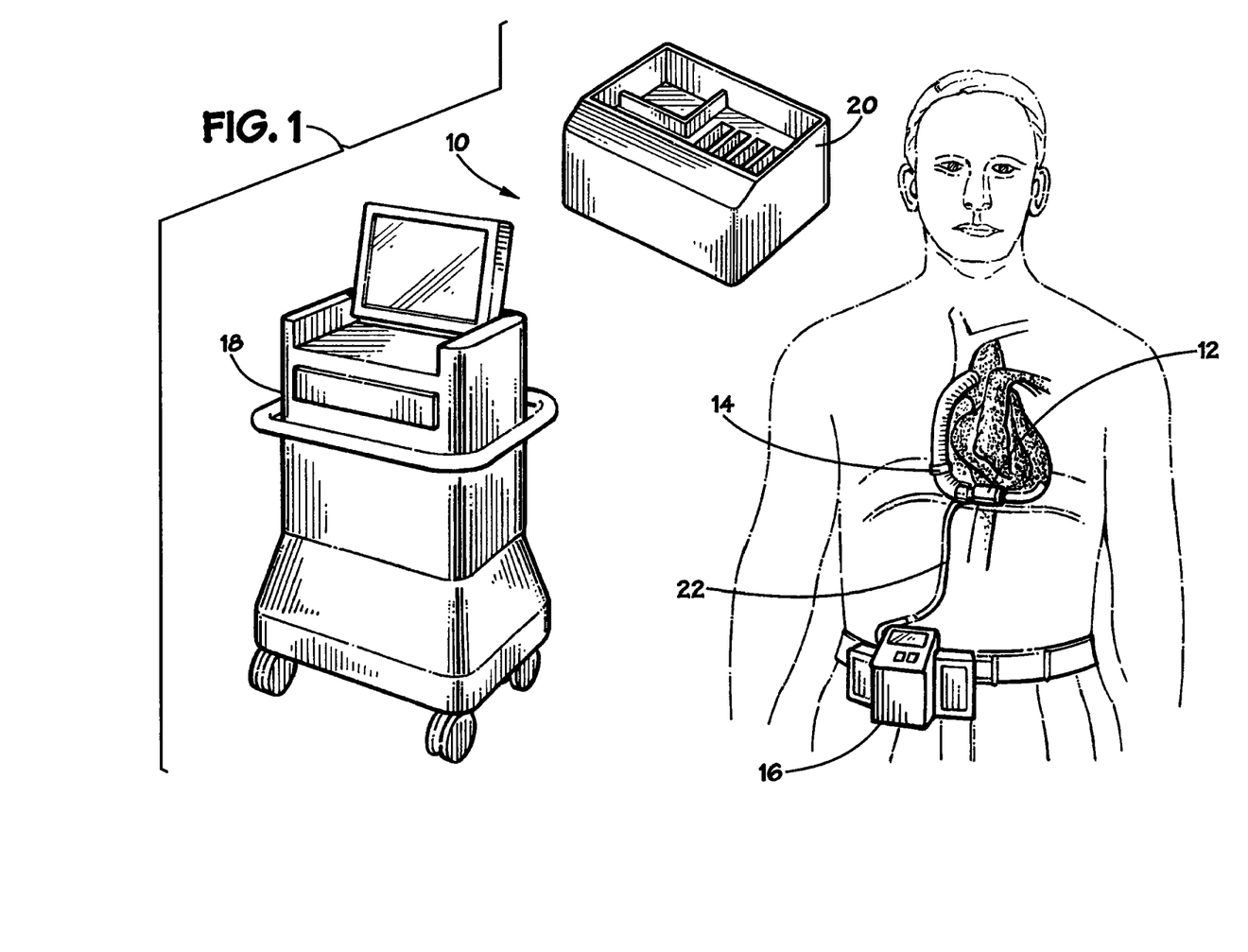
FIG. 1 schematically illustrates various components of an implantable pump system in accordance with embodiments of the present invention.

Turning to the figures, FIG. 1 illustrates a ventricle assist device (VAD) system 10 such as disclosed in U.S. Pat. No. 6,183,412, which is commonly assigned and incorporated herein by reference in its entirety. The VAD system 10 includes components designed for implantation within a human body and components external to the body. Implantable components include a rotary pump 12 and a flow sensor 14. The external components include a portable controller module 16, a clinical data acquisition system (CDAS) 18, and a patient home support system (PHSS) 20. The implanted components are connected to the controller module 16 via a percutaneous cable 22.

Figure 2:
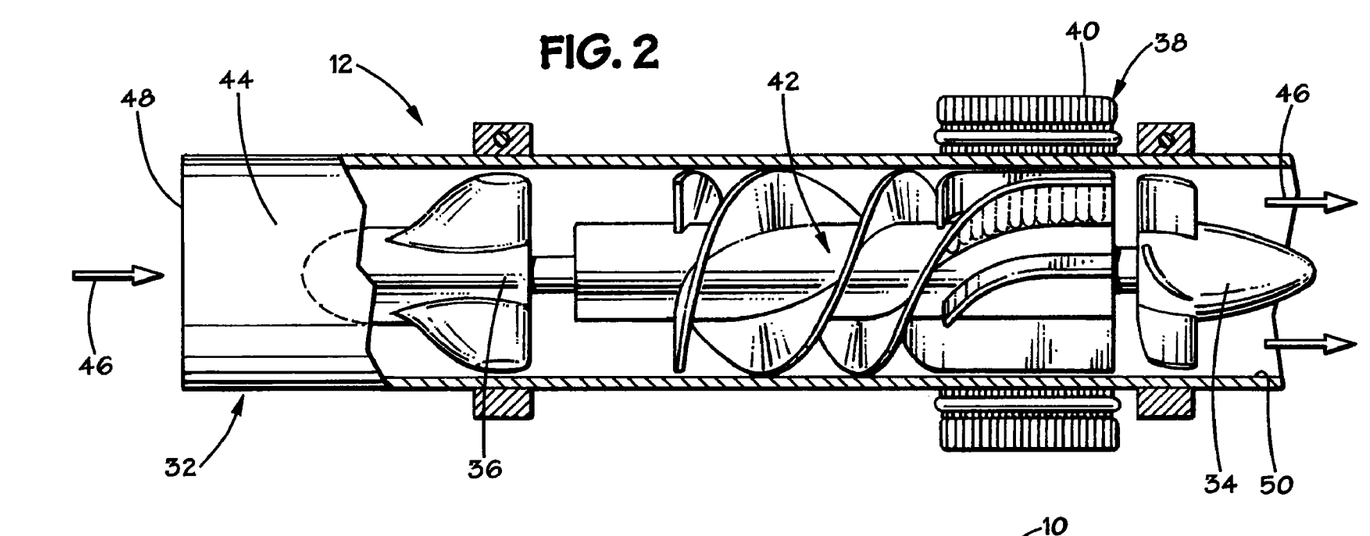
FIG. 2 is a cross-section view of an exemplary implantable pump in accordance with embodiments of the present invention.

The VAD System 10 may incorporate an implantable continuous-flow blood pump, such as the various embodiments of axial flow pumps disclosed in U.S. Pat. No. 5,527,159 or in U.S. Pat. No. 5,947,892, both of which are incorporated herein by reference in their entirety. An example of a blood pump suitable for use in an embodiment of the invention is illustrated in FIG. 2. The exemplary pump 12 includes a pump housing 32, a diffuser 34, a flow straightener 36, and a brushless DC motor 38, which includes a stator 40 and a rotor 42. The housing 32 includes a flow tube 44 having a blood flow path 46 therethrough, a blood inlet 48, and a blood outlet 50.

The stator 40 is attached to the pump housing 32, is preferably located outside the flow tube 44, and has a stator field winding 52 for producing a stator magnetic field. In one embodiment, the stator 40 includes three stator windings and may be three phase "Y" or "Delta" wound. The rotor 42 is located within the flow tube 44 for rotation in response to the stator magnetic field, and includes an inducer 58 and an impeller 60. Excitation current is applied to the stator windings 52 to generate a rotating magnetic field. A plurality of magnets 62 are coupled to the rotor 42. The magnets 62, and thus the rotor 42, follow the rotating magnetic field to produce rotary motion.

Figure 3:
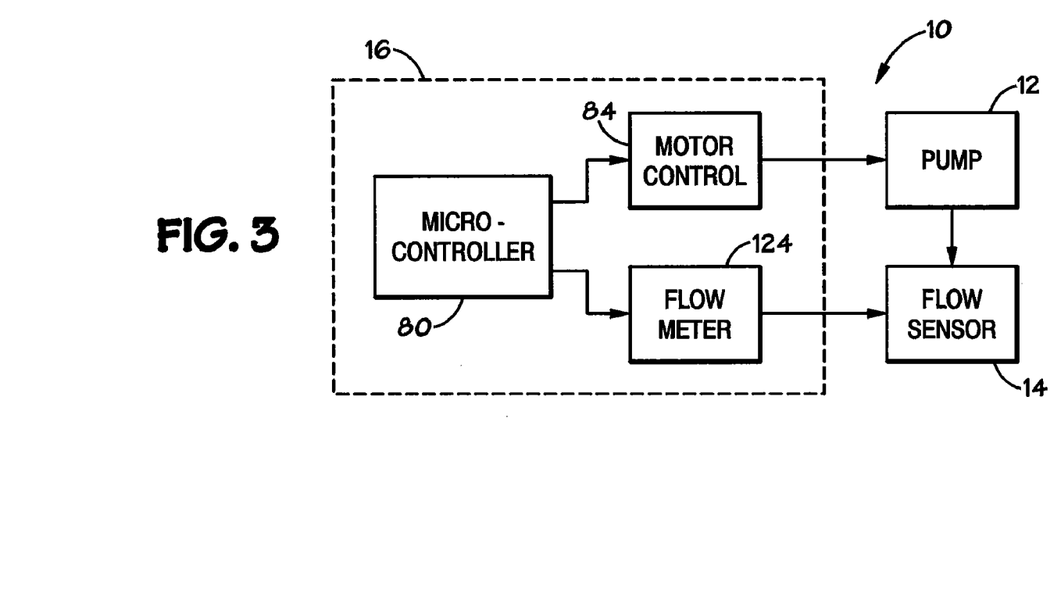
FIG. 3 is a block diagram illustrating aspects of a controller module in accordance with embodiments of the present invention.

FIG. 3 conceptually illustrates aspects of the pump system 10. More specifically, portions of the controller module 16 and the pump 12 are shown. The controller module 16 includes a processor, such as a microcontroller 80, which in one embodiment of the invention is a model PIC16C77 microcontroller manufactured by Microchip Technology. The microcontroller 80 includes a multiple channel analog to digital (A/D) converter, which receives indications of motor parameters from the motor controller 84. Thus, the controller module 16 may monitor parameters such as instantaneous motor current, motor voltage, and motor speed.

The embodiment shown in FIG. 3 further includes an integral flow meter 124. At least one flow sensor 14 is implanted down stream of the pump 12. Alternately, a flow sensor 14 may be integrated with the pump 12. The flow meter 124 is coupled between the implanted flow sensor 14 and the microcontroller 80. The flow meter 124 receives data from the flow sensor 14 and outputs flow rate data to the microcontroller 80, allowing the system to monitor instantaneous flow rate.

Since the implanted flow sensor 14 is coupled to the flow meter 124 of the controller module 16, a true measure of system performance (flow rate) is available for analysis, in addition to pump parameters such as motor speed and current (power). Further, since the flow meter 124 is an integral component of the controller module 16, flow rate may be displayed on the controller module display and flow rate data may be saved in the controller module memory.

In exemplary embodiments of the invention, the motor controller 84 comprises a MicroLinear ML4425 Motor Controller from Fairchild Semiconductor. The operation of the brushless DC motor 38 of the present invention requires that current be applied in a proper sequence to the stator windings 52 to create the rotating field. Two stator windings 52 have current applied to them at any one time, and by sequencing the current on and off to the respective stator windings 52, the rotating magnetic field is produced. In an embodiment of the invention, the motor controller 84 senses back electromotive force (EMF) voltage from the motor windings 52 to determine the proper commutation phase sequence using phase lock loop (PLL) techniques. Whenever a conductor, such as a stator winding 52, is "cut" by moving magnetic lines of force, such as are generated by the magnets 62 of the brushless DC motor 38, a voltage is induced. The voltage will increase with rotor speed 42. It is possible to sense this voltage in one of the three stator windings 52 because only two of the motor's windings 52 are activated at any one time, to determine the rotor 42 position.

An alternative method of detecting the rotor 42 position relative to the stator 40 for providing the proper stator winding 52 excitation current sequence is to use a position sensor, 5 such as a Hall effect sensor. Implementing aspects of the present invention using a motor with rotor position sensors, rather than a sensorless motor, would be a routine undertaking for one skilled in the art having the benefit of this disclosure. However, adding additional components, such as Hall effect sensors, requires additional space, which is limited in any implanted device application. Further, using a position detection device adds sources of system failures.

The motor controller 84 operates to maintain the pump 12 at an essentially constant speed regardless of the differential pressure across the pump or the flow through the pump. As noted above, the motor controller 84 uses a PLL to control the speed of the pump motor 38 (commutation control). An additional analog closed-loop control circuit controls the onboard pulse width modulator (PWM) to maintain a desired speed setting. Both control-loops work in unison to maintain proper speed control.

The motor controller 84 forms a PLL with a voltage-controlled oscillator (VCO), back-EMF sampling error amplifier, loop-filter, sequencer, and output driver. The motor controller 84 samples the instantaneous motor phase that is not energized to determine whether to increase or decrease the commutator (VCO) frequency. The VCO generates an output frequency (commutation rate) proportional to input voltage. A late commutation causes the error amplifier to charge the loop filter, increasing the VCO input while early commutation causes the error amplifier to discharge the loop filter, decreasing the VCO input. The PWM loop, operating at approximately 25 kHz in exemplary embodiments, effectively maintains the desired speed setting once the PLL has reached steady-state (the desired target speed). Constant speed control of the three-phase pump motor, under varying or pulsatile load conditions, is achieved by varying the amount of current delivered to the stator windings proportionally to the motor's load.

The commutation and PWM loops have, because of their associated filter networks, individual frequency and time domain responses associated with them. The frequency range over which the loop system will follow changes in the input frequency is called the lock-in range. The frequency range in which the loop acquires phase-lock is the capture range.

The dynamic characteristics of the phase-locked loop, and thus the way the pump motor responds to changes in load, are controlled primarily by the loop filter. The filter network included in the PLL serves two major functions. First, it removes any noise and high-frequency components from the error amplifer's output providing an average (dc) voltage to be fed to the VCO's input, and it is the primary element that determines the dynamic performance of the loop including capture (pull-in) range, lock-in range, bandwidth, and transient response.

Once the loop is phase-locked, the filter limits the speed of the loop to track changes in the input frequency (motor speed). In addition, the loop filter provides a "fly-wheel" effect, ensuring a rapid recapture of the signal if the system is thrown out of lock by a noise transient.

Variations in differential pressure across the pump 12 will impart instantaneous changes in the speed of the pump motor 38. The motor controller 84 will sense this change in speed through its back-EMF sampler and attempt to speed up or slow down the pump motor 38, such that the preset speed is maintained. This instantaneous load change and corresponding correction performed by the motor controller will result in a corresponding variation in the pump's current waveform, speed waveform, and flow waveform. An instantaneous increase in the pump's load will cause an instantaneous decrease in pump speed and thus an instantaneous increase in pump current and decrease in flow rate. Conversely, an instantaneous decrease in the pump's load will cause an instantaneous increase in pump speed and thus an instantaneous decrease in pump current and increase in flow rate.

Therefore, the pump's current (and therefore power), speed, and flow waveforms correlate well with changes in the pump's load. These waveforms may be used to calculate the patient's heart rate, instantaneous and mean blood flow rate, regurgitant flow, instantaneous and mean power consumption, the pump's efficiency, etc. These waveforms also indicate when the pump's speed is set too high and the ventricle begins to collapse. This condition exists when the flow and/or current waveforms are highly-asymmetric and/or their peaks appear to contain multiple ripples or are flattened (clipped). Additionally, waveforms with short negative rise-times (attack) followed by slower positive exponential fall-times (decay) indicate suction.

The aforementioned signals, current, speed, and flow, are time-continuous band-limited signals. The current signal is a composite signal containing the motor controller's PWM frequency, the patients heart rate (assuming the heart is beating), and other frequencies relating to certain physiologic responses within the patient's cardiovascular system (e.g. valve openings and closures, changes in systemic resistance, etc.). The pulse-width modulation frequency typically is approximately 25 kHz and the patient's heart rate is approximately 0.7 Hz to 4.0 Hz. A two-pole maximally flat low-pass Butterworth Filter ($f_c$=250 Hz) within the controller module 16 may be used to limit the bandwidth of this signal.

The power signal is the product of the pump motor current and pump motor voltage (a constant scalar) and is therefore a composite signal which, like the current, contains the motor controller's pulse-width modulation (PWM) frequency, the patients heart rate (assuming there is a heart rate), and other frequencies relating to certain physiologic responses within the patient's cardiovascular system (e.g. valve openings and closures, changes in systemic resistance, etc.). The pulse-width modulation frequency is approximately 25 kHz and the patient's heart rate is approximately 0.7 Hz to 4.0 Hz.

The speed signal typically contains the heart rate of the patient (assuming the heart is beating) as the dominant frequency along with other frequencies related to certain physiologic responses within the patient's cardiovascular system (e.g. valve openings and closures, changes in systemic pressure, etc.). The angular momentum of the rotor impeller and viscosity of the blood dampen abrupt changes in speed and thus the bandwidth of this signal is typically under 30 Hz.

The flow signal typically contains the heart rate of the patient (assuming the heart is beating) as the dominant frequency along with other frequencies related to certain physiologic responses within the patient's cardiovascular system (e.g. valve openings and closures, changes in systemic pressure, etc.). A two-pole maximally flat low-pass Butterworth Filter (currently with $f_c$=30 Hz) within the controller module 16 limits the bandwidth of this signal.

Embodiments of the present invention employ various mechanisms to detect the onset and/or presence of ventricular collapse based on the processing and/or analysis of certain inherent pump system parameters (e.g. flow, current, speed, etc.). These analysis techniques are performed in the time domain and frequency domain. Time domain mechanisms include correlation techniques as well as linear and non-linear signal processing. Frequency domain mechanisms include various real-time spectral analysis methods using Fourier Transforms such as the Fast Fourier Transform ("FFT") and the Discrete Fourier Transform ("DFT"), as well as other linear and non-linear signal processing techniques.

In the time domain, a physiologically appropriate flow(t) waveform is assumed to be quasi-sinusoidal at a single frequency proportional to the patient's native heart rate (i.e. fundamental frequency). In the frequency domain, the corresponding physiologically appropriate flow(f) waveform will be a single narrow spectral peak at the same single frequency proportional to the patient's native heart rate. As the flow(t) waveform becomes more distorted (i.e. deviates from a perfect sinusoid), the flow(f) waveform will contain additional spectral peaks corresponding to flow contributions at varying frequencies.

The Fourier Series may be used to compute the fundamental and harmonic components from time domain signals that are continuous and periodic. Many invivo waveforms that may denote suction, however, are not periodic, and further, the frequency components of such waveforms may not be harmonically related to the fundamental frequency. In accordance with aspects of the present invention, many frequency components, both harmonically related and not, about the fundamental are analyzed to precisely detect suction.

Figure 4:
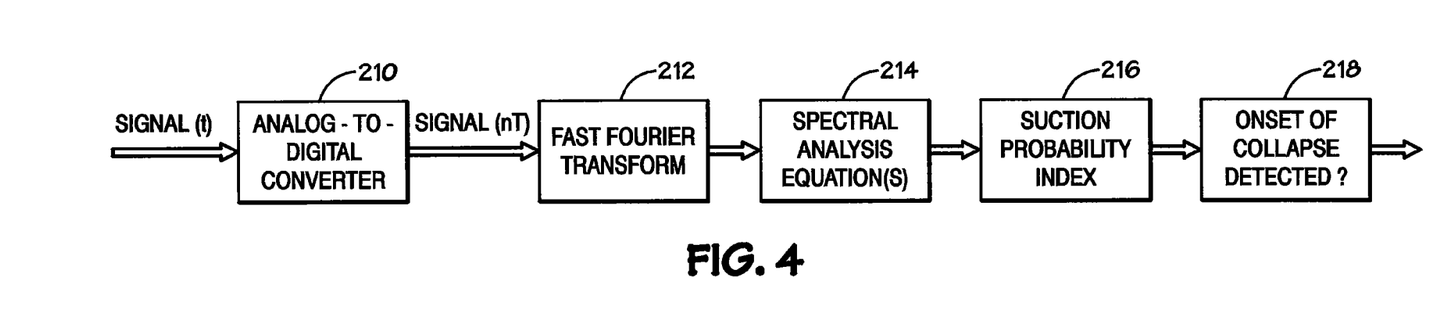
FIGS. 4–9 are block diagrams conceptually illustrating methods of detecting ventricle collapse in accordance with embodiments of the present invention.

FIG. 4 illustrates ventricular collapse methods based on a spectral analysis in accordance with embodiments of the present invention. The embodiments shown in block diagram form in FIG. 4 operate on the principle that the onset of ventricular collapse is imminent when the flow and/or current waveforms are asymmetric and/or their peaks appear to contain multiple ripples or are flattened (clipped). Variations in the flow, speed, current, and power waveforms in the time-domain will result in corresponding variation in their frequency-domain representations.

In block 210, one or more time-continuous band-limited signals are received and converted to a digital signal. In certain embodiments, the flow signal provided via the flow sensor 14 and flow meter 124 is specifically analyzed for suction detection, though one or more of the current, power, speed, etc. signals available may be used. The spectral content of the sampled signals are computed in block 212. A Fourier Transform such as the Discrete Fourier Transform ("DFT"), and/or Fast Fourier Transform ("FFT") may be used to obtain the frequency-domain responses for the signals converted in block 210.

The FFT is more efficient computationally than is the DFT and is more easily realized in hardware and/or software. Continuous conversion of the time-continuous signals from the time-domain to the frequency-domain provides real time spectral content information about these signals. Referring to FIG. 4, the array generated in block 212 is processed by spectral analysis equations in block 214 to generate a suction probability index in block 216, which may be expressed as a percentage. The suction probability index provides an indication of the imminence of ventricle collapse in block 218. Known methods to detect the onset or presence of ventricular collapse use a binary "suction detect" indicator when onset is discovered. No "suction indices" are used. The use of "suction indices" leads to a more precise diagnosis and gives the physician access to more information than a simple binary answer.

In accordance with embodiments of the invention, exemplary spectral analysis equations 214 used in various embodiments of the invention for processing the data to generate the suction probability index 216 include analyses based on harmonic distortion, total spectral distortion (harmonic distortion and noise), sub-fundamental distortion (distortion below the fundamental frequency), super-fundamental distortion (distortion above the fundamental frequency), the ratio of the super-fundamental distortion to the sub-fundamental distortion, super-physiologic distortion (distortion at frequencies above the assumed maximum physiologic fundamental frequency—typically 4 Hz or 240 BPM), and the spectral dispersion or "width" of the resulting flow(f) waveform. These spectral analysis techniques are addressed in detail as follows.

The spectral distortion factor measures the ratio of all energy contributed by all frequencies about the fundamental frequency with respect to the fundamental frequency. A higher distortion ratio indicates a higher probability of suction.

$$\text{Spectral distortion factor} = \frac{\left[\sqrt{\sum_{n=1}^{x}[A[f_{(n \cdot dF)}]]^2 - [A[f_1]]^2}\right] \cdot 100}{|A[f_1]|}$$

wherein n indicates the spectral component's index/position in the resulting array; x is the last index/position in this array; dF represents the frequency resolution/interval of the resulting FFT operation in Hertz; and $f_1$ is the fundamental frequency, the maximum (amplitude) spectral peak in the FFT resultant array. Since the spectral analysis of the flow rate signal pertains to the AC component, and not the offset, the range of interest does not include n=0 because the mean flow rate or DC component of the flow(f) waveform occurs at n=0. This is true for all of the frequency domain suction probability indices contained herein.

The harmonic distortion factor measures the ratio of energy contributed by all harmonics about the fundamental frequency with respect to the fundamental frequency.

$$\text{Harmonic distortion factor} = \frac{\left[\sqrt{\sum_{n=2}^{x}[A[f_n]]^2}\right] \cdot 100}{|A[f_1]|}$$

wherein n indicates the $n^{th}$ harmonic in the resulting array; x is the highest harmonic in this array; $f_1$ is the fundamental frequency, the maximum (amplitude) spectral peak in the FFT resultant array; and $f_n$ represents integer multiples of the fundamental $f_1$ from n=2 (second harmonic) to x ($x^{th}$ harmonic).

The sub-fundamental distortion factor measures the additive frequency contributions below the fundamental frequency with respect to the fundamental frequency.

$$\text{Sub-fundamental distortion factor} = \frac{\left[\sqrt{\sum_{n=1}^{n(f1)-1}[A[f_{(n \cdot dF)}]]^2}\right] \cdot 100}{|A[f_1]|}$$

wherein n indicates the spectral component's index/position in the resulting array; dF represents the frequency resolution/interval of the resulting FFT operation in Hertz; $f_1$ is the fundamental frequency, the maximum (amplitude) spectral peak in the FFT resultant array; and n(f1) is the index/position of the fundamental.

The super-fundamental distortion factor measures the additive frequency contributions above the fundamental frequency with respect to the fundamental frequency.

$$\text{Super-fundamental distortion factor} = \frac{\left[\sqrt{\sum_{n=n(f1)+1}^{x}[A[f_{(n \cdot dF)}]]^2}\right] \cdot 100}{|A[f_1]|}$$

wherein n indicates the spectral component's index/position in the resulting array; x is the last index/position in this array; dF represents the frequency resolution/interval of the resulting FFT operation in Hertz; $f_1$ is the fundamental frequency, the maximum (amplitude) spectral peak in the FFT resultant array; and n(f1) is the index/position of the fundamental.

The super/sub fundamental distortion factor measures the ratio of additive frequency contributions above the fundamental frequency to the additive frequency contributions below the fundamental frequency.

$$\text{Super/sub fundamental distortion factor} = \frac{\left[\sqrt{\sum_{n=n(f1)+1}^{x}[A[f_{(n \cdot dF)}]]^2}\right] \cdot 100}{\left[\sqrt{\sum_{n=1}^{n(f1)-1}[A[f_{(n \cdot dF)}]]^2}\right]}$$

wherein n indicates the spectral component's index/position in the resulting array; dF represents the frequency resolution/interval of the resulting FFT operation in Hertz; x is the last index/position in this array; and n(f1) is the index/position of the fundamental.

The super physiologic distortion factor measures the additive frequency contributions above the maximum expected physiologic frequency (i.e. 4 Hz=240 BPM) with respect to the fundamental frequency.

$$\text{Super physiologic distortion factor} = \frac{\left[\sqrt{\sum_{n=n(f_h)+1}^{x}[A[f_{(n \cdot dF)}]]^2}\right] \cdot 100}{|A[f_1]|}$$

wherein $f_h$ is a spectral peak at frequency=4 Hz; n indicates the spectral component's index/position in the resulting array; x is the last index/position in this array; dF represents the frequency resolution/interval of the resulting FFT operation in Hertz; $f_1$ is the fundamental frequency, the maximum (amplitude) spectral peak in the FFT resultant array.

In other embodiments, the spread of the waveform is measured. As noted above, it is assumed that a physiologically appropriate waveform in the time domain is quasi-sinusoidal at a single frequency proportional to the patient's native heart rate, and hence, the corresponding physiologically appropriate waveform in the frequency domain will be a singly narrow spectral peak at the same single frequency proportional to the patient's native heart rate. Deviations from this quasi-sinusoidal case may indicate suction as well as other defects.

For example, as the flow(t) waveform becomes more distorted, the flow(f) waveform will contain additional flow contributions at varying frequencies and will thus begin to "widen". The probability that suction is imminent or present increases proportionally to the width of flow(f). The measure of the width of flow(f) about the fundamental frequency is the square-root of the mean-squared variation about the fundamental frequency. The spectral dispersion factor measures the "width" of the flow(f), current(f), speed(f), and/or power(f) signals:

$$\text{Spread Flow} = \frac{\sqrt{\sum_{n=1}^{N} [A[f_{(n \cdot dF)}] - A[f_1]]^2}}{N}$$

wherein $f_1$ is the fundamental frequency, the maximum (amplitude) spectral peak in the FFT resultant array; dF represents the frequency resolution/interval of the resulting FFT operation in Hertz; n indicates the spectral component's index/position in the resulting array; and N is the last index/position in this array. Since the analysis of spread flow is concerned with the wave shape, and not the offset, the range of interest does not include n=0 because the mean flow rate or DC component of the flow(f) waveform occurs at n=0.

Figure 5:
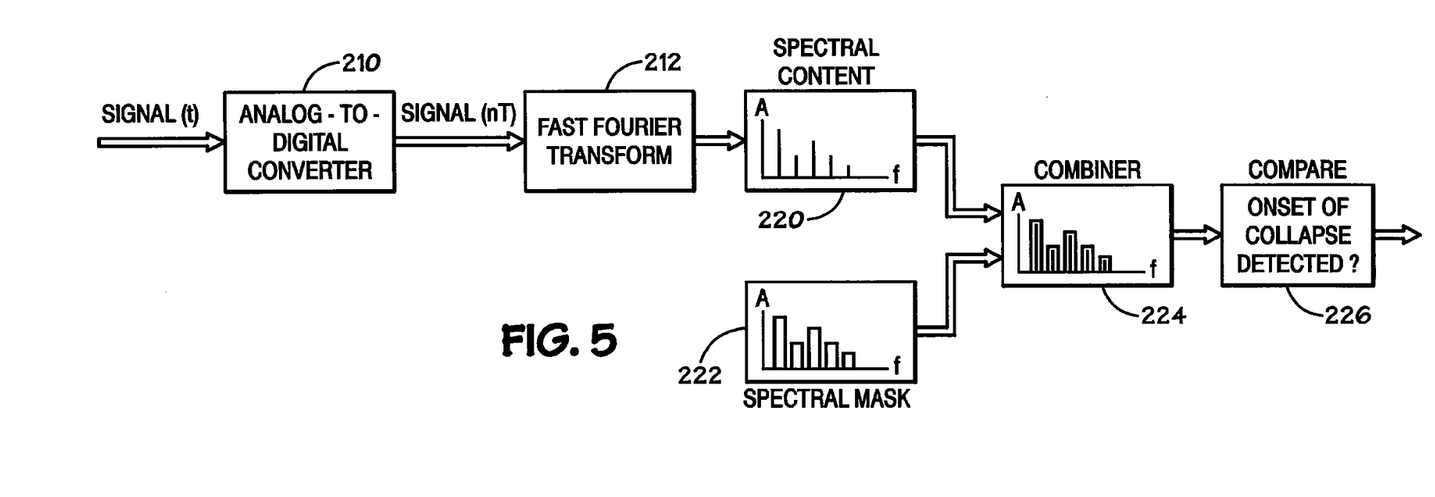
Figure 6:
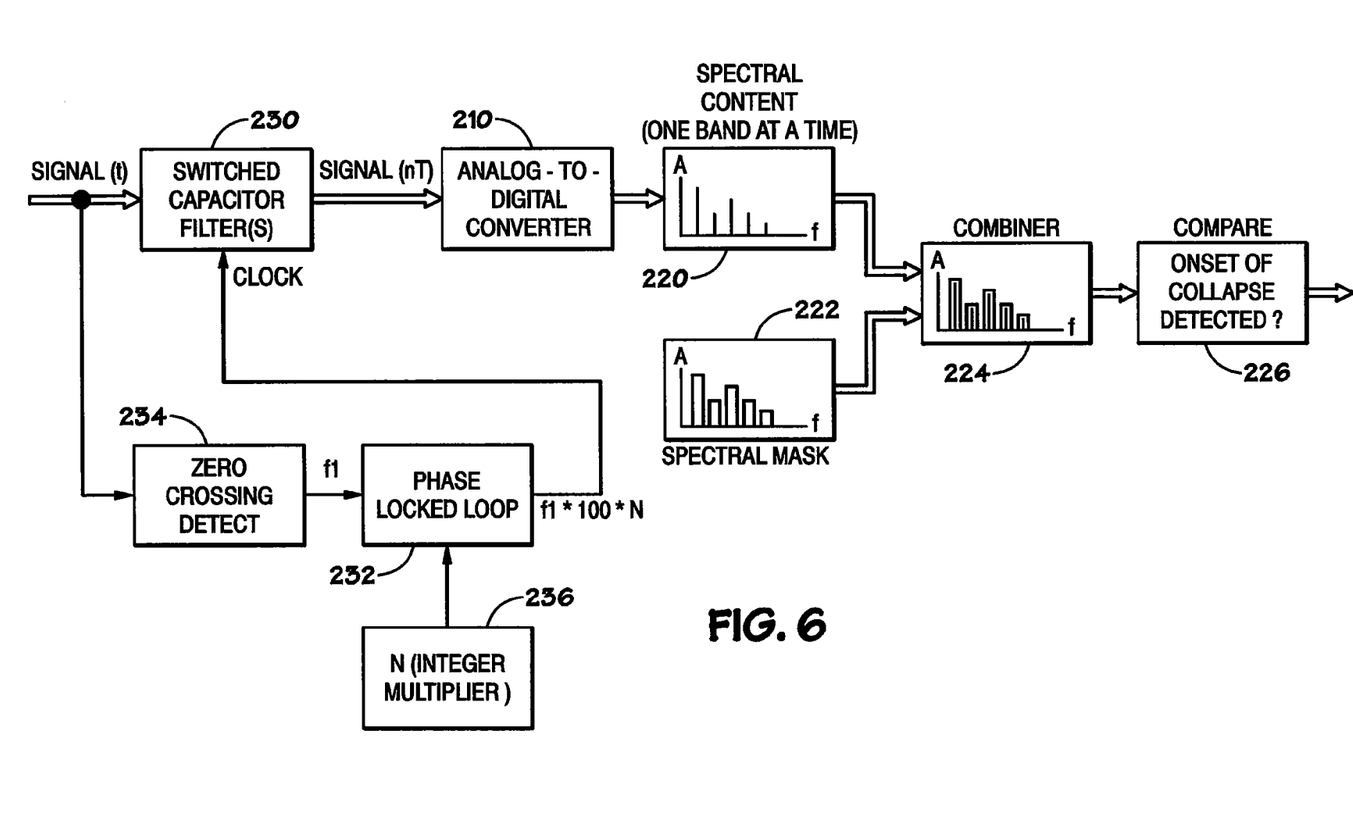

Some alternatives to applying the spectral content of the measured signal to spectral analysis equations are shown in FIGS. 5 and 6, where the real time spectral content measured signal is compared to a predetermined spectral mask. In the embodiment shown in FIG. 5, the spectral content 220 generated by the FFT 212 is compared to a predetermined spectral mask 222 in a combiner block 224. In block 226, the presence of suction is determined based on the comparison. The signals whose spectral components fall within the mask indicate suction and, conversely, signals whose spectral components fall outside the mask indicate normal flow.

In the embodiment shown in FIG. 6, the time domain responses are converted to frequency domain through the application of a synchronous switched-capacitor filter 230. In this exemplary embodiment, the frequency response of the filter 230 is controlled by a clock source one hundred times the desired pass-band frequency. A phase-locked loop 232 generates this clocking signal to the filter 230 by receiving the output from a zero crossing detector 234 and multiplying the incoming fundamental frequency by an integer multiplier 236, the value of which is selected by a digital input element such as a microcontroller. Incrementing the integer multiplier will cause the synchronous filter to "track" the incoming signal and output the spectral amplitude of the fundamental frequency, first harmonic, second harmonic, etc. The sum of the individual spectral amplitudes results in a frequency-domain representation of the time-domain signals.

As in the embodiment illustrated in FIG. 5, a comparison may then be made between the real-time spectral content 220 of these signals and the predetermined spectral mask 222. Signals whose spectral components fall within the mask indicate suction and, conversely, signals whose spectral components fall outside the mask indicate normal flow.

Figure 7:
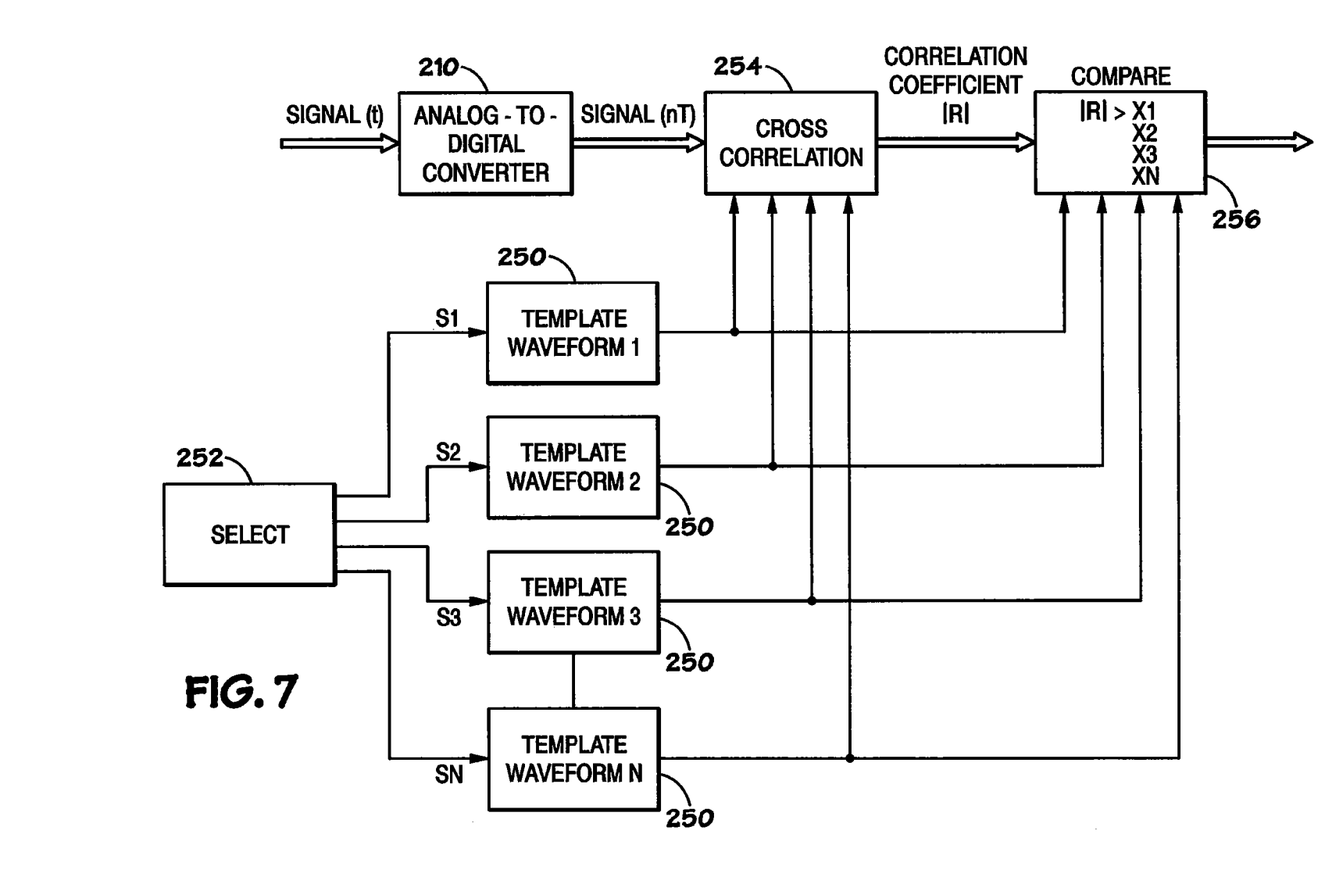

Other embodiments of the invention employ time domain analysis methods. FIG. 7 illustrates a method that cross-correlates the incoming time-sampled signal (for example, the flow or current signal) with predetermined time-domain waveforms 250 exemplifying the imminence of ventricular collapse. The waveforms 250 are selected in block 252 sequentially or based on the probability of occurrence in that particular patient derived experientially through clinical evaluation. A correlation coefficient is generated in block 254, where |R|=1 signifies a perfect "match" and |R|=0 indicates no correlation at all. The correlation coefficient is compared to predetermined thresholds in block 256 to derive a suction probability index. If the calculated correlation coefficient exceeds a predetermined value, ventricular collapse is imminent. Conversely, if the calculated correlation coefficient is below the predetermined value, suction is not present.

Alternatively, the incoming time-sampled signal may be cross-correlated with time-domain representations of sine waves at integer multiples of the incoming fundamental frequency. The sum of the individual spectral amplitudes results in a frequency-domain representation of the time-domain signals. A comparison is then made between the real-time spectral content of these signals and a predetermined spectral mask as in the embodiments shown in FIGS. 5 and 6. Signals whose spectral components fall within the mask indicate suction and, conversely, signals whose spectral components fall outside the mask indicate normal flow.

Still further analysis methods continuously time-sample signals representing system parameters such as flow, speed, current, or power, and calculate the slope between a series of data points. By comparing the calculated slope to a predetermined value, ventricular collapse may be detected. This may also be applied to the first or second derivatives of the flow, current, speed, and/or power signals.

Figure 8:
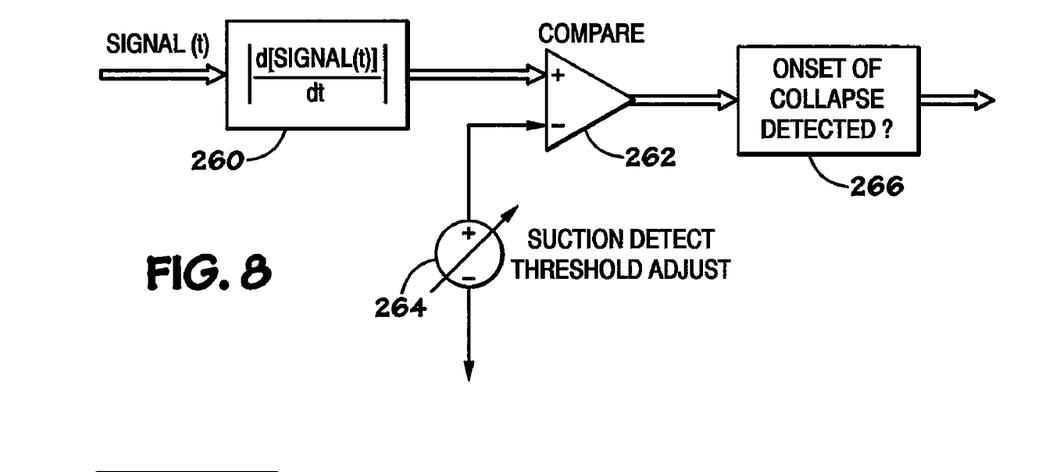

More specifically, as shown in bock diagram form in FIG. 8, the derivative of the time-sampled signal, such as flow, with respect to time is calculated in block 260, which yields blood acceleration. Therefore, a large negative dflow(t)/dt indicates the presence of ventricular collapse. The calculated derivative is provided as one input to a comparitor 262. An adjustable suction detect threshold value 264 is provided as the second input to the comparitor 262 such that the derivative calculated in block 260 is compared to a predetermined value. Based on the output of the comparitor 262, the presence of collapse is determined in block 266.

Figure 9:
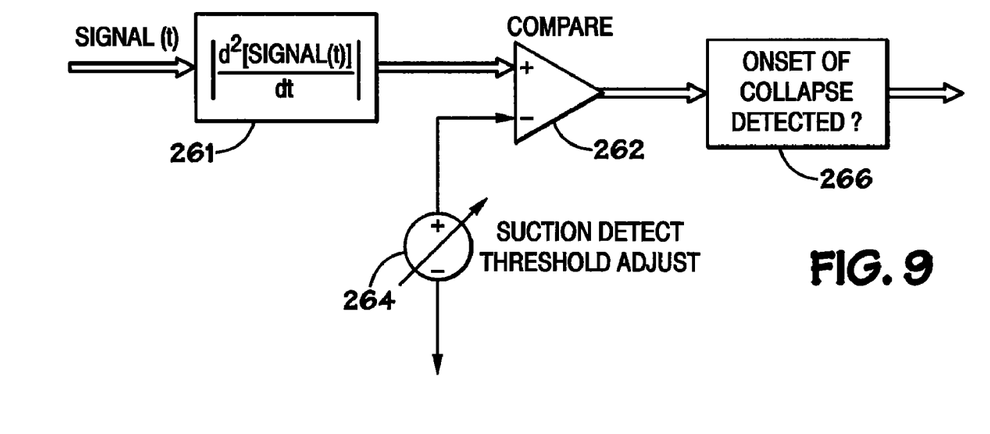

Similarly, as shown in FIG. 9, the second derivative of the measured parameter (e.g. $d^2 \text{flow}(t)/dt^2$, $d^2 \text{current}(t)/dt^2$, $d^2 \text{power}(t)/dt^2$, or $d^2 \text{speed}(t)/dt^2$) is calculated in block 261 and compared to a predetermined value to detect suction based on changes in the aforementioned signals.

In various embodiments of the invention, the aforementioned methods for detecting the imminence of ventricular collapse are implemented in software, hardware, or both. Software implementations include using the microcontroller 80 used provided in the controller module 16. Alternatively, a stand-alone microcontroller or a digital signal processor ("DSP"), for example, may be used. Exemplary hardware implementations may include a field programmable gate array ("FPGA"), a complex programmable logic device ("CPLD"), application specific integrated circuits ("ASIC"), discrete analog and/or digital components, etc.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of detecting ventricular collapse in a patient having a blood pump implanted, the method comprising:
   sampling a time-based system parameter of the blood pump;
   analyzing the time-based system parameter; and
   calculating a suction probability index in response to the analysis of the time-based system parameter that provides an indication of the imminence of ventricle collapse.

2. The method of claim 1, wherein sampling a time-based system parameter of the blood pump includes sampling the pump current.

3. The method of claim 1, wherein sampling a time-based system parameter of the blood pump includes sampling the pump speed.

4. The method of claim 1, wherein the implantable pump includes a flow sensing device providing an indication of the flow rate through the pump, and wherein sampling a time-based system parameter of the blood pump includes sampling the flow rate.

5. The method of claim 1, further comprising converting the sampled time-based parameter to a digital signal.

6. The method of claim 1, further comprising computing the spectral content of the sampled time-based signal.

7. The method of claim 6, further comprising applying the computed spectral content to a spectral analysis equation to calculate the suction probability index.

8. The method of claim 7, wherein analyzing the time-based system parameter includes computing the total distortion of the time-based system parameter waveform.

9. The method of claim 8, wherein computing the spectral content includes applying a Fourier Transform, and wherein the suction probability index is calculated according to $$\text{suction probability index} = \frac{\left[\sqrt{\sum_{n=1}^{x}[A[f_{(n \cdot dF)}]]^2 - [A[f_1]]^2}\right] \cdot 100}{|A[f_1]|}$$

wherein A represents amplitude, n indicates the position of the spectral component in the array resulting from the Fourier Transform; x is the last position in the array; dF represents the frequency resolution/interval of the Fourier Transform in Hertz; and $f_1$ is the fundamental frequency, maximum (amplitude) spectral peak in the array.

10. The method of claim 7, wherein analyzing the time-based system parameter includes computing the harmonic distortion of the time-based system parameter waveform.

11. The method of claim 10, wherein computing the spectral content includes applying a Fourier Transform, and wherein the suction probability index is calculated according to $$\text{suction probability index} = \frac{\left[\sqrt{\sum_{n=2}^{x}[A[f_n]]^2}\right] \cdot 100}{|A[f_1]|}$$

wherein A represents amplitude, n indicates the $n^{th}$ harmonic in the array resulting from the Fourier Transform; x is the last position in the array; $f_1$ is the fundamental frequency, the maximum (amplitude) spectral peak in the FFT resultant array; and $f_n$ represents integer multiples of the fundamental $f_1$ from n=2 (second harmonic) to x ($x^{th}$ harmonic).

12. The method of claim 7, wherein analyzing the time-based system parameter includes computing the distortion of the time-based system parameter waveform below the fundamental frequency.

13. The method of claim 12, wherein computing the spectral content includes applying a Fourier Transform, and wherein the suction probability index is calculated according to:

$$\text{suction probability index} = \frac{\left[\sqrt{\sum_{n=1}^{n(f1)-1}[A[f_{(n \cdot dF)}]]^2}\right] \cdot 100}{|A[f_1]|}$$

wherein A represents amplitude, n indicates the position of the spectral component in the array resulting from the Fourier Transform; dF represents the frequency resolution of the Fourier Transform in Hertz; $f_1$ is the fundamental frequency, the maximum (amplitude) spectral peak in the Fourier Transform resultant array; and n(f1) is the position of the fundamental frequency in the array.

14. The method of claim 7, wherein analyzing the time-based system parameter includes computing the distortion of the time-based system parameter waveform above the fundamental frequency.

15. The method of claim 14, wherein computing the spectral content includes applying a Fourier Transform, and wherein the suction probability index is calculated according to:

$$\text{suction probability index} = \frac{\left[\sqrt{\sum_{n=n(f1)+1}^{x}[A[f_{(n \cdot dF)}]]^2}\right] \cdot 100}{|A[f_1]|}$$

wherein A represents amplitude, n indicates the position of the spectral component in the array resulting from the Fourier Transform; x is the last position in the array; dF represents the frequency resolution/interval of the Fourier Transform in Hertz; $f_1$ is the fundamental frequency, the maximum (amplitude) spectral peak in the array; and n(f1) is the position of the fundamental frequency in the array.

16. The method of claim 14, wherein computing the spectral content further includes computing the ratio of additive frequency contributions above the fundamental frequency to the additive frequency contributions below the fundamental frequency, and wherein the suction probability index is calculated according to:

$$\text{suction probability index} = \frac{\left[\sqrt{\sum_{n=n(f1)+1}^{x}[A[f_{(n\cdot dF)}]]^2}\right] \cdot 100}{\left[\sqrt{\sum_{n=1}^{n(f1)-1}[A[f_{(n\cdot dF)}]]^2}\right]}$$

wherein A represents amplitude, n indicates the position of the spectral component in the array resulting from the Fourier Transform; x is the last position in the array; dF represents the frequency resolution/interval of the Fourier Transform in Hertz; $f_1$ is the fundamental frequency, the maximum (amplitude) spectral peak in the array; and n(f1) is the position of the fundamental frequency in the array.

17. The method of claim 7, wherein analyzing the time-based system parameter includes computing the distortion of the time-based system parameter waveform above a predetermined physiologic frequency.

18. The method of claim 17, wherein computing the spectral content includes applying a Fourier Transform, and wherein the suction probability index is calculated according to:

$$\text{suction probability index} = \frac{\left[\sqrt{\sum_{n=n(f_h)+1}^{x}[A[f_{(n\cdot dF)}]]^2}\right] \cdot 100}{|A[f_1]|}$$

wherein A represents amplitude, $f_h$ is a spectral peak at the predetermined physiologic frequency; n indicates the position of the spectral component in the array resulting from the Fourier Transform; x is the last position in the array; dF represents the frequency resolution/interval of the Fourier Transform in Hertz; $f_1$ is the fundamental frequency, the maximum (amplitude) spectral peak in the resultant array.

19. The method of claim 7, wherein analyzing the time-based system parameter includes computing the spread of the time-based system parameter waveform.

20. The method of claim 19, wherein computing the spectral content includes applying a Fourier Transform, and wherein the suction probability index is calculated according to:

$$\text{suction probability index} = \frac{\sqrt{\sum_{n=1}^{N}[A[f_{(n\cdot dF)}] - A[f_1]]^2}}{N}$$

wherein A represents amplitude, $f_1$ is the maximum (amplitude) spectral peak in the array resulting from the Fourier Transform; dF represents the frequency resolution/interval of the Fourier Transform in Hertz; n indicates the position of the spectral component in the array; and N is the last position in the array.

21. The method of claim 6, further comprising comparing the computed spectral content to a predetermined spectral mask to calculate the suction probability index.

22. The method of claim 19, wherein computing the spectral content includes applying a Fourier Transform.

23. The method of claim 19, wherein computing the spectral content includes applying the sampled time-based signal to a synchronous switched-capacitor filter.

24. The method of claim 1, wherein analyzing the time-based system parameter includes calculating the slope of the time-based system parameter.

25. The method of claim 24, wherein calculating the suction probability index includes comparing the slope to a predetermined value.

26. The method of claim 24, wherein calculating the slope includes calculating the first derivative of the time-based parameter.

27. The method of claim 24, wherein calculating the slope includes calculating the second derivative of the time-based parameter.

28. A control system for an pump system, the control system comprising:
a processor having inputs for receiving a signal representing a time-based parameter of the pump system;
the processor being programmed to analyze the time-based system parameter and in response to the analysis, calculate a suction probability index that provides an indication of the imminence of ventricle collapse.

29. The control system of claim 28, wherein the time-based parameter includes the pump system current.

30. The control system of claim 28, wherein the time-based parameter includes the pump system flow rate.

31. A pump system, comprising:
an pump including a motor having a rotor and a stator, the stator including a plurality of stator windings;
a motor controller coupled to the motor;
a processor having inputs coupled to the motor controller for receiving a signal representing a time-based parameter of the pump;
the processor being programmed to analyze the time-based system parameter and calculate a suction probability index that provides an indication of the imminence of ventricle collapse.

32. The pump system of claim 31, wherein the motor controller applies current to the stator windings in a sequence to create a rotating field; and wherein the time-based parameter includes the stator winding current.

33. The pump system of claim 31, further comprising an implantable flow sensing device coupled to the processor for providing a signal representing the pump flow rate, wherein the time-based parameter includes the pump flow rate.

34. A pump system, comprising:
an pump including a motor having a rotor and a stator, the stator including a plurality of stator windings;
a motor controller coupled to the motor;
means coupled to the motor controller for analyzing a time-based parameter of the pump calculating a suction probability index that provides an indication of the imminence of ventricle collapse.

* * * * *